(12) United States Patent
Choi et al.

(10) Patent No.: US 7,888,453 B2
(45) Date of Patent: Feb. 15, 2011

(54) FERROCENE-CONTAINING POLYMERS AND ORGANIC MEMORY DEVICES COMPRISING THE SAME

(75) Inventors: Tae Lim Choi, Seongnam-si (KR); Kwang Hee Lee, Suwon-si (KR); Sang Kyun Lee, Seongnam-si (KR); Won Jae Joo, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 595 days.

(21) Appl. No.: 11/633,021

(22) Filed: Dec. 4, 2006

(65) Prior Publication Data
US 2007/0197768 A1 Aug. 23, 2007

(30) Foreign Application Priority Data
Feb. 22, 2006 (KR) .................. 10-2006-0017155

(51) Int. Cl.
*C08G 79/00* (2006.01)
(52) U.S. Cl. ..................................................... 528/395
(58) Field of Classification Search .................. 528/395
See application file for complete search history.

(56) References Cited

U.S. PATENT DOCUMENTS 5,272,238 A * 12/1993 Garnier et al. .................. 528/9
5,416,170 A    5/1995  Rhee et al.
6,944,047 B2   9/2005  Rotenberg et al.
7,307,338 B1  12/2007  Mandell et al.
2002/0163057 A1 11/2002 Bulovic et al.
2004/0027849 A1  2/2004 Yang et al.
2004/0227136 A1 11/2004 Lan et al.
2004/0250849 A1 12/2004 Chen et al.
2007/0197768 A1  8/2007 Choi et al.

FOREIGN PATENT DOCUMENTS

JP          62-095882        5/1987

OTHER PUBLICATIONS

Knapp et al., Polymer 39(13), 1998, p. 5828.*
Lee et al., Bull. Korean Chem. Soc. 2000, 21(8), p.759.*

* cited by examiner

*Primary Examiner*—Randy Gulakowski
*Assistant Examiner*—Shane Fang
(74) *Attorney, Agent, or Firm*—Harness, Dickey & Pierce, P.L.C.

(57) ABSTRACT

Disclosed herein are ferrocene-containing polymers in which ferrocene is conjugated to the backbone of conductive conjugated polymers. Further disclosed are organic memory devices comprising the ferrocene-containing polymers. Because the organic memory devices possess the advantages of decreased switching time, decreased operating voltage, decreased fabrication costs and increased reliability, they may be used as highly integrated large-capacity memory devices.

14 Claims, 3 Drawing Sheets

FERROCENE-CONTAINING POLYMERS AND ORGANIC MEMORY DEVICES COMPRISING THE SAME

PRIORITY STATEMENT

This non-provisional application claims priority under 35 U.S.C. §119 to Korean Patent Application No. 10-2006-0017155, filed on Feb. 22, 2006, in the Korean Intellectual Property Office (KIPO), the entire contents of which are herein incorporated by reference.

BACKGROUND

1. Field

Example embodiments relate to ferrocene-containing polymers and organic memory devices using the polymers. Other example embodiments relate to ferrocene-containing polymers in which ferrocene is conjugated to the backbone of conductive conjugated polymers, and organic memory devices including the ferrocene-containing polymers.

2. Description of the Related Art

With the recent dramatic developments in digital communication technology, demand for a variety of memory devices has been increasing rapidly. Memory devices suitable for use in applications including, for example, portable computers and electronic devices, including mobile terminals, smart cards, electronic money, digital cameras, personal digital assistants (PDAs), digital audio players and/or multimedia players, are required for retaining data in memory even when no power is being applied to the memory device, thereby tending to reduce the memory-related power consumption of the device.

Conventional memory devices may include a bistable element that may be switched between a higher resistance state and a lower resistance state when a voltage is applied to the devices. Resistive memory devices are memories whose resistance is varied depending on an applied voltage and in which data is stored in response to changes in the resistance.

Chalcogenide materials, semiconductors and various types of oxides and nitrides are known to have resistive memory properties. Some organic materials are also found to have resistive memory properties. Of these resistive memory devices, organic memory devices may include an upper electrode, a lower electrode and a memory layer between the upper and lower electrodes, wherein the memory layer may be formed of an organic material and memory properties are realized by using bistability of resistance values obtained when a voltage is applied between the upper and lower electrodes. Next-generation organic memory devices ensure non-volatility, which is an advantage of conventional flash memories, and at the same time, overcome the disadvantages of undesirable processability, increased fabrication costs and decreased degree of integration.

Research has been done on various materials due to their potential use as materials for organic active layers of organic memory devices. One example of such an organic memory device utilizes an organic memory device including an upper electrode, a lower electrode and a selectively conductive media between the two electrodes wherein the selectively conductive media contains an organic layer and a passive layer and the organic layer is made of a conjugated organic material. Another example includes a molecular memory cell including a first electrode, a second electrode, and first and second charge storage molecules between the first and second electrodes and coupled to the electrodes by a molecular linkage. Other work has suggested a conductive polymeric composite for use as an electrode material of a secondary battery, the polymeric composite including a salt of a ferrocene derivative and a polypyrrole or its derivative.

Ferrocene and its derivatives are currently being investigated for their inherent electrical, optical and magnetic properties. However, a major portion of research on ferrocenes and its derivatives has been devoted to their use as fuel additives and polymerization catalysts. There hasn't been any research on the use of ferrocenes and its derivatives as materials for active layers of organic memory devices.

SUMMARY

Therefore, example embodiments are provided below for addressing certain of the deficiencies and/or limitations of the related art, and example embodiments provide ferrocene-containing polymers that may offer many potential benefits when used as materials for organic active layers of organic memory devices. Example embodiments provide highly integrated large-capacity organic memory devices including the ferrocene-containing polymers that possess the advantages of decreased switching time, decreased operating voltage, decreased fabrication costs and increased reliability.

In accordane with example embodiments, there are provided ferrocene-containing polymers represented by Formulae 1 and 2 below:

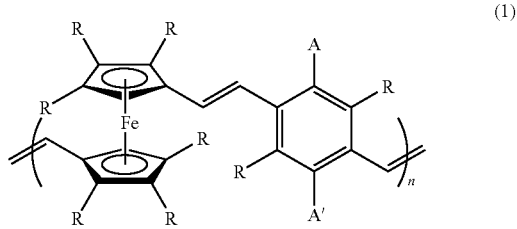

(1)

wherein each R, which may be identical or different, is $C_{1-20}$ alkyl, $C_{3-20}$ cycloalkyl, $C_{5-30}$ heterocycloalkyl, $C_{2-20}$ alkenyl, $C_{6-20}$ aryl, $C_{5-30}$ heteroaryl, $C_{7-20}$ arylalkyl or $C_{7-30}$ heteroarylalkyl, A and A' are independently a hydrogen atom, $C_{1-20}$ alkyl, $C_{3-20}$ cycloalkyl, $C_{5-30}$ heterocycloalkyl, $C_{2-20}$ alkenyl, $C_{6-20}$ aryl, $C_{5-30}$ heteroaryl, $C_{7-20}$ arylalkyl, $C_{7-30}$ heteroarylalkyl or OR' (in which R' is $C_{1-20}$ alkyl, $C_{3-20}$ cycloalkyl, $C_{5-30}$ heterocycloalkyl, $C_{2-20}$ alkenyl, $C_{6-20}$ aryl, $C_{5-30}$ heteroaryl, $C_{7-20}$ arylalkyl or $C_{7-30}$ heteroarylalkyl), and n is from 1 to 1000; and

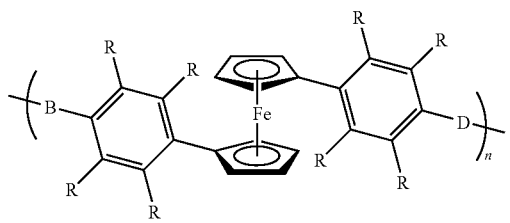

(2)

wherein each R, which may be identical or different, is $C_{1-20}$ alkyl, $C_{3-20}$ cycloalkyl, $C_{5-30}$ heterocycloalkyl, $C_{2-20}$ alkenyl, $C_{6-20}$ aryl, $C_{5-30}$ heteroaryl, $C_{7-20}$ arylalkyl or $C_{7-30}$ heteroarylalkyl, B is a hydrogen atom, a $C_{1-20}$ alkyl group, a substituted or unsubstituted $C_{5-20}$ aromatic group, a substituted or unsubstituted $C_{5-20}$ heteroaromatic group containing at least one heteroatom selected from O, S and N atoms, the aromatic and heteroaromatic groups capable of being substituted with at least one substituent selected from $C_{1-12}$ alkyl, vinyl, alkoxy, ester, carboxyl, thiol and amine groups, D is a substituted or unsubstituted $C_{5-30}$ aromatic group or a substituted or unsubstituted $C_{5-20}$ heteroaromatic group containing at least one heteroatom selected from O, S and N atoms, the aromatic and heteroaromatic groups capable of being substituted with at least one substituent selected from $C_{1-12}$ alkyl, vinyl, alkoxy, ester, carboxyl, thiol and amine groups, and n is from 1 to 1000.

In accordance with example embodiments, there are provided organic memory devices including the ferrocene-containing polymers. The organic memory devices of example embodiments may include a first electrode, a second electrode and an organic active layer between the first and second electrodes, wherein the organic active layer may be formed of the ferrocene-containing polymer of Formula 1 or 2.

In accordance with example embodiments, a method of fabricating an organic memory device may include providing a first electrode, forming an organic active layer formed of a ferrocene-containing polymer represented by Formula 1 or 2 below:

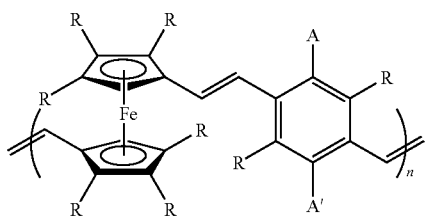

(1)

wherein each R, which is identical or different, is $C_{1-20}$ alkyl, $C_{3-20}$ cycloalkyl, $C_{5-30}$ heterocycloalkyl, $C_{2-20}$ alkenyl, $C_{6-20}$ aryl, $C_{5-30}$ heteroaryl, $C_{7-20}$ arylalkyl or $C_{7-30}$ heteroarylalkyl, A and A' are independently a hydrogen atom, $C_{1-20}$ alkyl, $C_{3-20}$ cycloalkyl, $C_{5-30}$ heterocycloalkyl, $C_{2-20}$ alkenyl, $C_{6-20}$ aryl, $C_{5-30}$ heteroaryl, $C_{7-20}$ arylalkyl, $C_{7-30}$ heteroarylalkyl or OR' (in which R' is $C_{1-20}$ alkyl, $C_{3-20}$ cycloalkyl, $C_{5-30}$ heterocycloalkyl, $C_{2-20}$ alkenyl, $C_{6-20}$ aryl, $C_{5-30}$ heteroaryl, $C_{7-20}$ arylalkyl or $C_{7-30}$ heteroarylalkyl), and n is from 1 to 1000; or

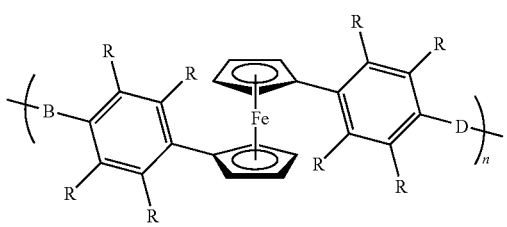

(2)

wherein each R, which is identical or different, is $C_{1-20}$ alkyl, $C_{3-20}$ cycloalkyl, $C_{5-30}$ heterocycloalkyl, $C_{2-20}$ alkenyl, $C_{6-20}$ aryl, $C_{5-30}$ heteroaryl, $C_{7-20}$ arylalkyl or $C_{7-30}$ heteroarylalkyl, B is a hydrogen atom, a $C_{1-20}$ alkyl group, a substituted or unsubstituted $C_{5-20}$ aromatic group, a substituted or unsubstituted $C_{5-20}$ heteroaromatic group containing at least one heteroatom selected from O, S and N atoms, the aromatic and heteroaromatic groups capable of being substituted with at least one substituent selected from $C_{1-12}$ alkyl, vinyl, alkoxy, ester, carboxyl, thiol and amine groups, D is a substituted or unsubstituted $C_{5-30}$ aromatic group or a substituted or unsubstituted $C_{5-20}$ heteroaromatic group containing at least one heteroatom selected from O, S and N atoms, the aromatic and heteroaromatic groups capable of being substituted with at least one substituent selected from $C_{1-12}$ alkyl, vinyl, alkoxy, ester, carboxyl, thiol and amine groups, and n is from 1 to 1000 on the first electrode and forming a second electrode on the organic active layer.

BRIEF DESCRIPTION OF THE DRAWINGS

Example embodiments will be more clearly understood from the following detailed description taken in conjunction with the accompanying drawings.

FIG. 1 is a schematic cross-sectional view of an organic memory device according to example embodiments;

FIG. 2 shows diagrams illustrating the mechanism by which a novel ferrocene-containing polymer of example embodiments shows bistability;

FIG. 3 is a schematic perspective view of a memory matrix according to example embodiments;

FIG. 4 is a graph showing the current-voltage (I-V) characteristics of an organic memory device fabricated in Example 1 of example embodiments; and FIG. 5 is a graph showing the resistance-voltage characteristics of an organic memory device fabricated in Example 1 of example embodiments.

DESCRIPTION OF EXAMPLE EMBODIMENTS

Figure 1:
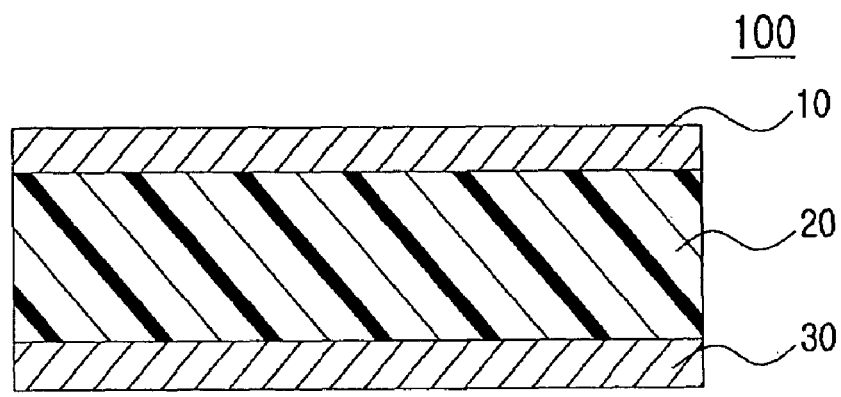
FIGS. 1-5 represent non-limiting, example embodiments as described herein.

Example embodiments will now be described in greater detail with reference to the accompanying drawings. In the drawings, the thicknesses of layers and regions may be exaggerated for clarity. Detailed illustrative example embodiments are disclosed herein. Specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but on the contrary, example embodiments are to cover all modifications, equivalents, and alternatives falling within the scope of example embodiments. Like numbers refer to like elements throughout the description of the figures.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the scope of example embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between" and/or "adjacent" versus "directly adjacent").

The terminology used herein is for the purpose of describing particular embodiments only and is not intended to be limiting of example embodiments. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the scope of example embodiments.

Spatially relative terms, such as "beneath", "below", "lower", "above", "upper" and the like, may be used herein for ease of description to describe one element or a feature's relationship to another element or feature as illustrated in the Figures. It will be understood that the spatially relative terms are intended to encompass different orientations of the device in use or operation in addition to the orientation depicted in the Figures. For example, if the device in the Figures is turned over, elements described as "below" or "beneath" other elements or features would then be oriented "above" the other elements or features. Thus, for example, the term "below" can encompass both an orientation which is above as well as below. The device may be otherwise oriented (rotated 90 degrees or viewed or referenced at other orientations) and the spatially relative descriptors used herein should be interpreted accordingly.

Example embodiments are described herein with reference to cross-sectional illustrations that are schematic illustrations of idealized embodiments (and intermediate structures). As such, variations from the shapes of the illustrations as a result, for example, of manufacturing techniques and/or tolerances, may be expected. Thus, example embodiments should not be construed as limited to the particular shapes of regions illustrated herein but may include deviations in shapes that result, for example, from manufacturing. For example, an implanted region illustrated as a rectangle may have rounded or curved features and/or a gradient (e.g., of implant concentration) at its edges rather than an abrupt change from an implanted region to a non-implanted region. Likewise, a buried region formed by implantation may result in some implantation in the region between the buried region and the surface through which the implantation may take place. Thus, the regions illustrated in the figures are schematic in nature and their shapes do not necessarily illustrate the actual shape of a region of a device and do not limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Example embodiments are related to ferrocene-containing polymers in which ferrocene is conjugated to the backbone of conductive conjugated polymers. Specifically, the ferrocene-containing polymers are represented by Formulae 1 and 2 below:

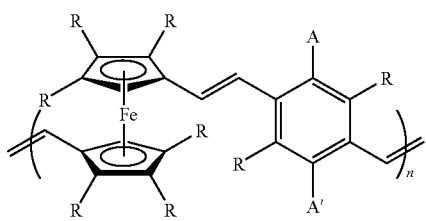

(1)

wherein each R, which may be identical or different, is $C_{1-20}$ alkyl, $C_{3-20}$ cycloalkyl, $C_{5-30}$ heterocycloalkyl, $C_{2-20}$ alkenyl, $C_{6-20}$ aryl, $C_{5-30}$ heteroaryl, $C_{7-20}$ arylalkyl or $C_{7-30}$ heteroarylalkyl, A and A' are independently a hydrogen atom, $C_{1-20}$ alkyl, $C_{3-20}$ cycloalkyl, $C_{5-30}$ heterocycloalkyl, $C_{2-20}$ alkenyl, $C_{6-20}$ aryl, $C_{5-30}$ heteroaryl, $C_{7-20}$ arylalkyl, $C_{7-30}$ heteroarylalkyl or OR' (in which R' is $C_{1-20}$ alkyl, $C_{3-20}$ cycloalkyl, $C_{5-30}$ heterocycloalkyl, $C_{2-20}$ alkenyl, $C_{6-20}$ aryl, $C_{5-30}$ heteroaryl, $C_{7-20}$ arylalkyl or $C_{7-30}$ heteroarylalkyl), and n is from 1 to 1000; and

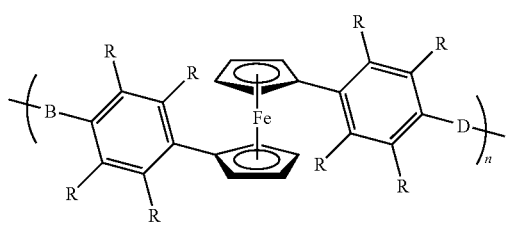

(2)

wherein each R, which may be identical or different, is $C_{1-20}$ alkyl, $C_{3-20}$ cycloalkyl, $C_{5-30}$ heterocycloalkyl, $C_{2-20}$ alkenyl, $C_{6-20}$ aryl, $C_{5-30}$ heteroaryl, $C_{7-20}$ arylalkyl or $C_{7-30}$ heteroarylalkyl, B is a hydrogen atom, a $C_{1-20}$ alkyl group, a substituted or unsubstituted $C_{5-20}$ aromatic group, a substituted or unsubstituted $C_{5-20}$ heteroaromatic group containing at least one heteroatom selected from O, S and N atoms, the aromatic and heteroaromatic groups capable of being substituted with at least one substituent selected from $C_{1-12}$ alkyl, vinyl, alkoxy, ester, carboxyl, thiol and amine groups, D is a substituted or unsubstituted $C_{5-30}$ aromatic group or a substituted or unsubstituted $C_{5-20}$ heteroaromatic group containing at least one heteroatom selected from O, S and N atoms, the aromatic and heteroaromatic groups capable of being substituted with at least one substituent selected from $C_{1-12}$ alkyl, vinyl, alkoxy, ester, carboxyl, thiol and amine groups, and n is from 1 to 1000.

Specific examples of alkyl groups may include straight-chained and/or branched alkyl groups, e.g., methyl, ethyl, propyl, isobutyl, sec-butyl, tert-butyl, pentyl, iso-amyl and/or hexyl.

The term "cycloalkyl" as used herein refers to a monovalent monocyclic system having about 5 to about 30 carbon atoms. At least one hydrogen atom contained in the cycloalkyl group may be substituted. The term "heterocycloalkyl group" as used herein refers to a $C_5$-$C_{30}$ monovalent monocyclic system containing one to three heteroatoms selected from N, O, P and S atoms. At least one hydrogen atom contained in the heterocycloalkyl group may be substituted.

The term "aryl" as used herein refers to a carbocyclic aromatic system including one or more aromatic rings in which the rings may be attached together in a pendent manner or may be fused. Specific examples of the aryl group may include aromatic groups, e.g., phenyl, naphthyl, and/or tetrahydronaphthyl. At least one hydrogen atom contained in the aryl group may be substituted. The term "heteroaryl" as used herein refers to a $C_5$-$C_{30}$ cyclic aromatic system containing one to three heteroatoms selected from N, O, P and S atoms in which the rings may be attached together in a pendent manner or may be fused. At least one hydrogen atom contained in the heteroaryl group may be substituted.

The term "arylalkyl" as used herein refers to a group in which a part of hydrogen atoms contained in the aryl group defined above are substituted with lower alkyl radicals, e.g., methyl, ethyl and/or propyl. Examples of the arylalkyl group may include benzyl and phenylethyl. At least one hydrogen atom contained in the arylalkyl group may be substituted.

The term "heteroarylalkyl" as used herein refers to a group in which a part of hydrogen atoms contained in the heteroaryl group defined above are substituted with lower alkyl radicals, e.g., methyl, ethyl and/or propyl.

Ferrocene-containing polymers that may be represented by Formula 1 are those represented by Formulae 3 and 4 below:

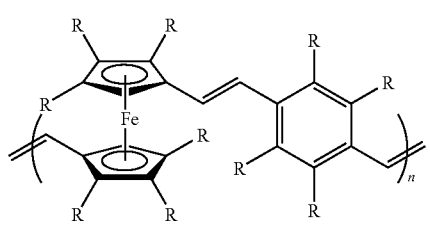

(3)

wherein each R, which may be identical or different, is $C_{1-20}$ alkyl, $C_{3-20}$ cycloalkyl, $C_{5-30}$ heterocycloalkyl, $C_{2-20}$ alkenyl, $C_{6-20}$ aryl, $C_{5-30}$ heteroaryl, $C_{7-20}$ arylalkyl or $C_{7-30}$ heteroarylalkyl, and n is from 1 to 1000; and

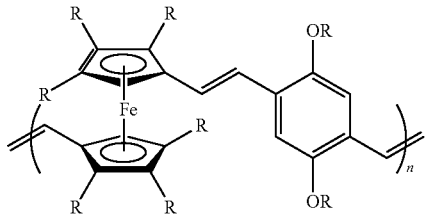

(4)

wherein each R, which may be identical or different, is $C_{1-20}$ alkyl, $C_{3-20}$ cycloalkyl, $C_{5-30}$ heterocycloalkyl, $C_{2-20}$ alkenyl, $C_{6-20}$ aryl, $C_{5-30}$ heteroaryl, $C_{7-20}$ arylalkyl or $C_{7-30}$ heteroarylalkyl, and n is from 1 to 1000.

Alternatively, the ferrocene-containing polymers of example embodiments may have structures represented by Formulae 5 through 7 below:

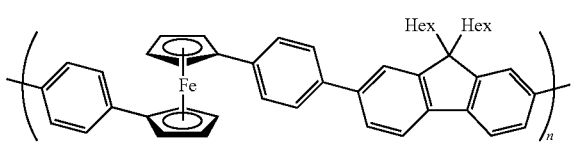

(5)

wherein Hex represents a hexyl group and n is from 1 to 1000;

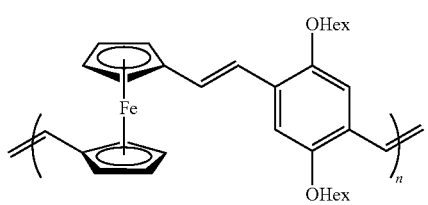

(6)

wherein Hex represents a hexyl group and n is from 1 to 1000; and

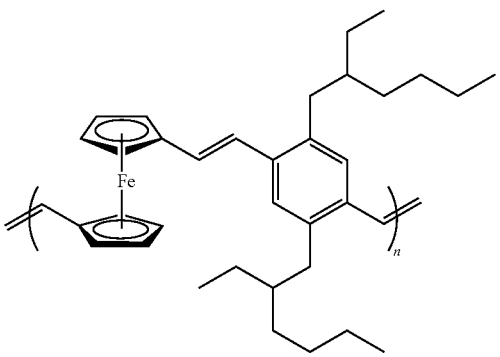

(7)

wherein n is from 1 to 1000.

The ferrocene-containing polymer of Formula 2 may have a structure represented by one of Formulae 8 through 11 below:

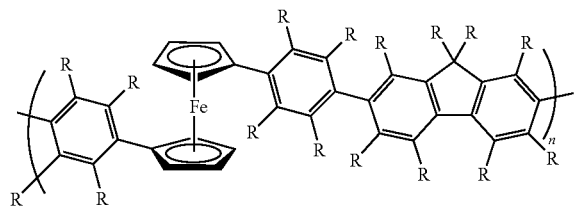

(8)

wherein each R, which may be identical or different, is $C_{1-20}$ alkyl, $C_{3-20}$ cycloalkyl, $C_{5-30}$ heterocycloalkyl, $C_{2-20}$ alkenyl, $C_{6-20}$ aryl, $C_{5-30}$ heteroaryl, $C_{7-20}$ arylalkyl or $C_{7-30}$ heteroarylalkyl, and n is from 1 to 1000;

(9)

wherein each R, which may be identical or different, is $C_{1-20}$ alkyl, $C_{3-20}$ cycloalkyl, $C_{5-30}$ heterocycloalkyl, $C_{2-20}$ alkenyl, $C_{6-20}$ aryl, $C_{5-30}$ heteroaryl, $C_{7-20}$ arylalkyl or $C_{7-30}$ heteroarylalkyl, and n is from 1 to 1000;

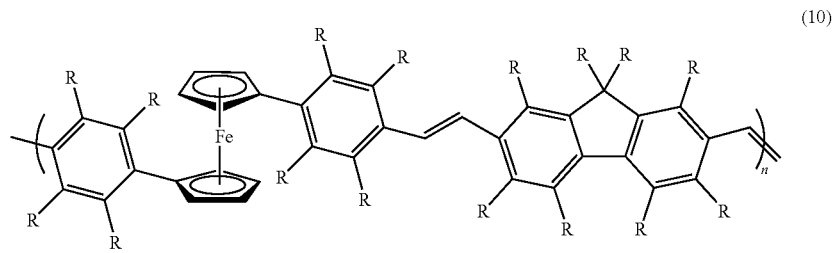

(10)

wherein each R, which may be identical or different, is $C_{1-20}$ alkyl, $C_{3-20}$ cycloalkyl, $C_{5-30}$ heterocycloalkyl, $C_{2-20}$ alkenyl, $C_{6-20}$ aryl, $C_{5-30}$ heteroaryl, $C_{7-20}$ arylalkyl or $C_{7-30}$ heteroarylalkyl, and n is from 1 to 1000; and

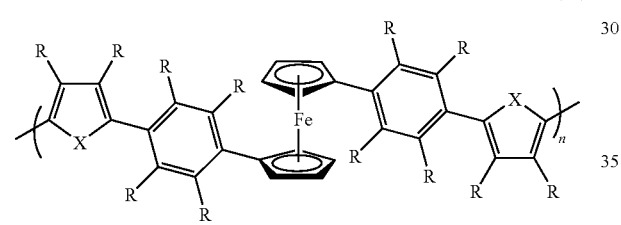

(11)

wherein each R, which may be identical or different, is $C_{1-20}$ alkyl, $C_{3-20}$ cycloalkyl, $C_{5-30}$ heterocycloalkyl, $C_{2-20}$ alkenyl, $C_{6-20}$ aryl, $C_{5-30}$ heteroaryl, $C_{7-20}$ arylalkyl or $C_{7-30}$ heteroarylalkyl, each X is O, S or N, and n is from 1 to 1000.

Methods for synthesizing the ferrocene-containing polymers of example embodiments will be explained. Many reactions may be carried out to incorporate ferrocene into the backbone of polymers. For example, the polymers of Formulae 5 to 7 may be synthesized by the following methods.

1. Synthesis of Ferrocene-Containing Polymer of Formula 5

The ferrocene-containing polymer of Formula 5 may be synthesized as depicted in Reaction Scheme 1. First, 1,1'-ferrocene diboronic acid pinacol ester and 1,4-bromoiodobenzene may be subjected to Suzuki coupling in the presence of a Pd catalyst to give 1,1'-bis(p-bromophenyl)ferrocene as a monomer. The monomer may be polycondensed with another monomer, e.g., 9,9-di(2'-ethylhexyl)fluorene-2,7-diboronic acid, by the Suzuki reaction to afford the ferrocene-containing polymer (1) of Formula 5.

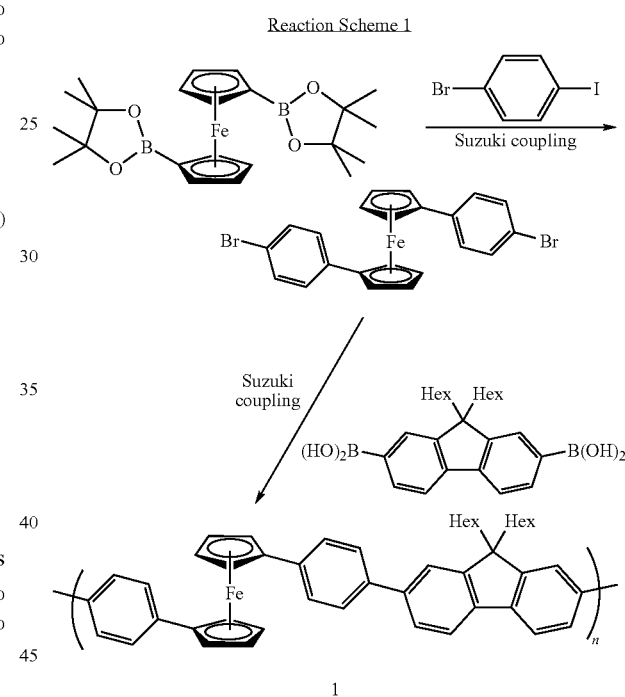

2. Synthesis of Ferrocene-Containing Polymer of Formula 6

The ferrocene-containing polymer of Formula 6 may be synthesized by the Horner-Emmons reaction as depicted in Reaction Scheme 2, which is a reaction in which an aldehyde is coupled with a diethyl phosphonate under basic conditions to form a C—C double bond. The C—C double bond thus formed may have a trans configuration. A monomer used herein may be 1,4-bis(diethyl(2,5-hexyloxy)benzylphosphonate) having hexyl chains as pendant groups, which act to improve the solubility of polymers. The addition of potassium butoxide as a base to the monomer may lead to deprotonation of the monomer, and as a result, a reactive yield may be formed. Further addition of 1,1'-ferrocene dicarboxyaldehyde may lead to formation of another C—C double bond, thus affording the ferrocene-containing polymer (2) of Formula 6.

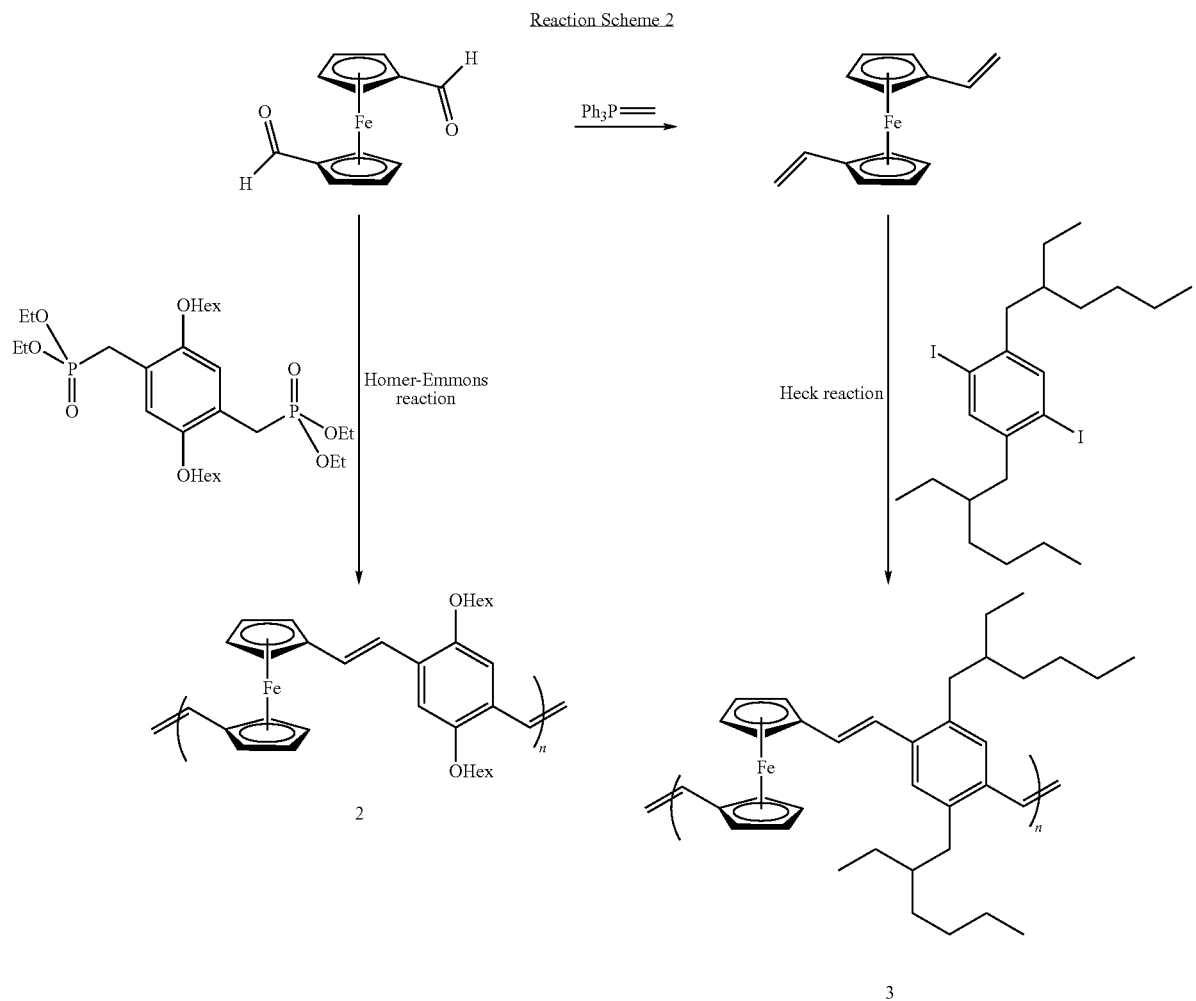

Reaction Scheme 2

3. Synthesis of Ferrocene-Containing Polymer of Formula 7

The ferrocene-containing polymer of Formula 7 may be prepared by coupling an aryl halide with a vinyl group via a Heck reaction. 1,1'-divinylferrocene may be prepared from 1,1-ferrocene dicarboxylaldehyde, which is used above, by the Wittig reaction. A base may be added to methyltriphenylphophonium iodide, and after about 30 minutes, 1,1'-ferrocene dicarboxylaldehyde may be added thereto to give 1,1'-divinyl ferrocene as a monomer. The monomer may be mixed with 1,4-bis(2-ethylhexyl)-2,5-diiodobenzene, followed by the addition of a Pd catalyst to cause the Heck polycondensation, affording the polymer 3. The branched long alkyl chains in the polymer may contribute to improvement in the solubility of the polymer.

Example embodiments are related to organic memory devices including the ferrocene-containing polymers. The organic memory devices of example embodiments may include a first electrode, a second electrode and an organic active layer between the first and second electrodes, wherein the organic active layer may be formed of the ferrocene-containing polymer of Formula 1 or 2.

FIG. 1 is a schematic cross-sectional view of an organic memory device according to example embodiments. With reference to FIG. 1, the organic memory device of example embodiments may include a first electrode 10, a second electrode 30 and an organic active layer 20 between the first and second electrodes 10 and 30. The resistance values of the organic active layer 20 obtained when a voltage is applied to the memory device 100 may show bistability, thus achieving memory properties of the memory device.

Figure 2:
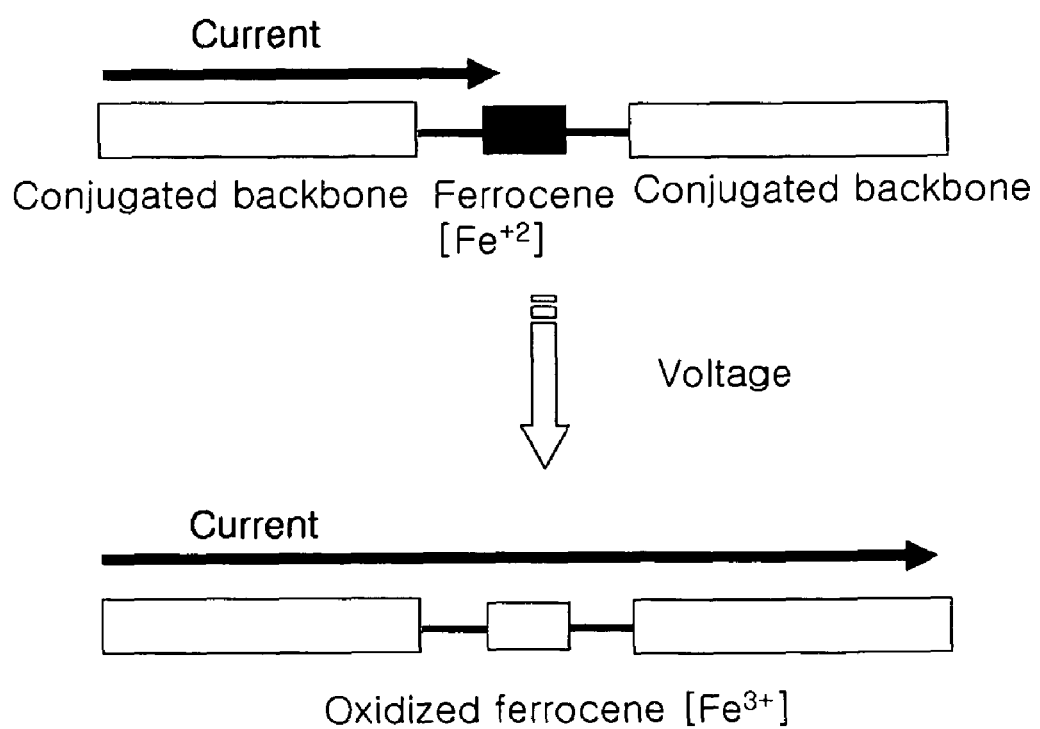

FIG. 2 shows diagrams illustrating the operating mechanism of an organic memory device according to example embodiments. The ferrocene-containing polymers of example embodiments may have multiple oxidation states, which may be set by the application of a proper voltage. Because conjugated polymer moieties linked to ferrocene exhibit electron accepting nature, the ferrocene-containing conductive polymers of example embodiments may have several redox potentials. The application of a particular voltage may remove one or more electrons from the ferrocene-containing conductive polymers to change the oxidation states. The oxidation state of the memory device set by the application of a particular voltage may remain unchanged until another voltage is applied.

The state wherein the ferrocene-containing polymers contain $Fe^{2+}$ may become a higher resistance state (e.g., a less conductive state), and the state wherein the ferrocene-containing polymers contain $Fe^{3+}$, which is an oxidation state of $Fe^{2+}$, may become a lower resistance state (e.g., a more conductive state). When a proper electrical voltage is applied between the two electrodes of the memory device according to example embodiments, the organic active layer may switch between a higher resistance state and a lower resistance state. Assuming that the lower resistance state is defined as data "1" and the higher resistance state is defined as data "0", two logic states of the data may be stored. Accordingly, the states may be maintained even when no power is being applied to the memory device, thus ensuring non-volatility of the organic memory device.

The organic memory device may be fabricated on a substrate. As the substrate, a common organic and/or inorganic substrate may be used, e.g., a flexible substrate. Examples of suitable materials for the substrate may include glass, silicon, surface-modified glass, polypropylene, activated acrylamide ceramics, membranes, gels and/or aerogels. The first electrode 10 and the second electrode 30 may be made of at least one electrically conductive material selected from the group consisting of metals, metal alloys, metal nitrides, metal oxides, metal sulfides, conductive polymers, organic conductors, nanostructures and/or crystals. Specific examples of materials for the first and second electrodes may include, but are not limited to, gold, silver, platinum, copper, cobalt, nickel, tin, titanium, tungsten, aluminum and/or indium tin oxide.

Specific examples of conductive polymers that may be used as the electrode materials may include polyphenylacetylene-based polymers (e.g., polydiphenylacetylene, poly(t-butyl)diphenylacetylene, poly(trifluoromethyl)diphenylacetylene, poly(bistrifluoromethyl)acetylene, polybis(t-butyldiphenyl)acetylene, poly(trimethylsilyl)diphenylacetylene, poly(carbazole)diphenylacetylene, polydiacetylene, polyphenylacetylene, polypyridineacetylene, polymethoxyphenylacetylene, polymethylphenylacetylene, poly(t-butyl)phenylacetylene, polynitrophenylacetylene, poly(trifluoromethyl)phenylacetylene, poly(trimethylsilyl)phenylacetylene and/or derivatives thereof) and/or polythiophene-based polymers.

The organic memory devices of example embodiments may further include a barrier layer formed under the first electrode or on the second electrode to prevent or reduce damage to the first or second electrode due to attacks by the organic materials. The barrier layer may be formed of a material selected from the group consisting of $SiO_x$, $AlO_x$, $NbO_x$, $TiO_x$, $CrO_x$, $VO_x$, $TaO_x$, $CuO_x$, $MgO_x$, $WO_x$ and/or $AlNO_x$, and may be formed of a material selected from the group consisting of $SiO_2$, $Al_2O_3$, $Cu_2O$, $TiO_2$ and/or $V_2O_3$. The barrier layer may also be formed of an organic material (e.g., Alq3, polymethylmethacrylate, polystyrene and/or PET). The barrier layer may have a thickness of about 20 Å to about 300 Å.

Figure 3:
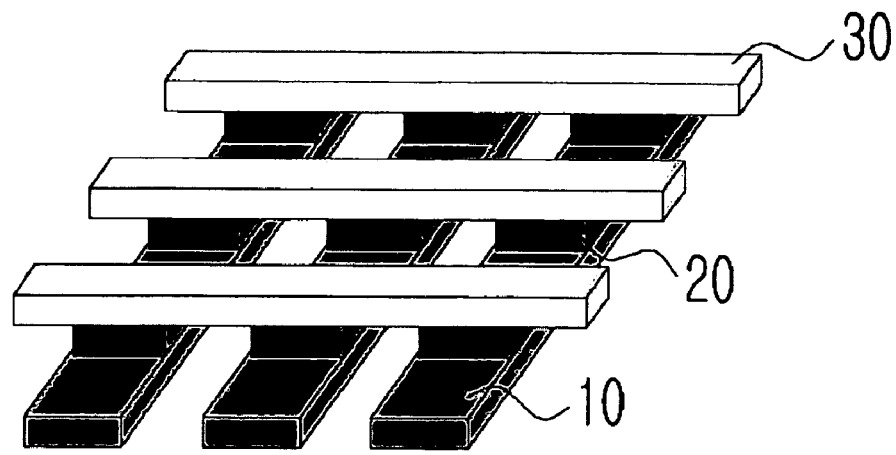

FIG. 3 is a schematic perspective view of an exemplary memory matrix employing the memory device of example embodiments. As shown in FIG. 3, the memory matrix may be formed on a suitable substrate (e.g., a glass and/or silicon substrate). With this configuration of the memory matrix, a plurality of cells may be formed at intersections between first electrodes 10 and second electrodes 30. The cells thus formed may provide bistability characteristics.

The organic memory devices of example embodiments may be well suited for use in computers, portable information devices, cell phones, medical devices, radar devices and/or satellite devices. Because the organic memory devices of example embodiments may be smaller in size and weight, they may be used to improve the portability of portable digital devices, including cell phones, PDAs, notebook computers, digital cameras, portable multimedia players and/or DMB terminals.

The organic memory devices of example embodiments may be fabricated by any method known in the art to which example embodiments pertain. The use of the ferrocene-containing polymers according to example embodiments may enable formation of the organic active layers by simpler and economical techniques, for example, spin casting and/or spin coating, without involving an increased cost technique, for example, electron beam evaporation, in terms of processing and materials.

The ferrocene-containing polymers of example embodiments may be coated on a second electrode (i.e. a lower electrode), which may be formed on a substrate by deposition, to form an organic active layer. Coating processes for the formation of the organic active layer are not particularly limited, and examples thereof may include spin casting, spin coating, spray coating, electrostatic coating, dip coating, blade coating, roll coating and/or ink-jet printing. The organic active layer may have a thickness of about 50 Å to about 3,000 Å.

At least one solvent selected from the group consisting of chloroform, N-methylpyrrolidone, acetone, cyclopentanone, cyclohexanone, methyl ethyl ketone, ethyl cellosolve acetate, butyl acetate, ethylene glycol, toluene, xylene, tetrahydrofuran, dimethylformamide, chlorobenzene, 1,2-dichloroethane, acetonitrile and mixtures thereof, may be used to form the organic active layer by spin coating. A solvent system or mixture of two or more of the solvents in any miscible ratio may also be used.

The first and second electrodes may be formed by known coating processes, including deposition, e.g., thermal evaporation, sputtering, e-beam evaporation and/or spin coating.

Hereinafter, example embodiments will be explained in more detail with reference to the following examples. However, these examples are given for the purpose of illustration and are not to be construed as limiting the scope of example embodiments.

EXAMPLES

Preparative Example 1

About 100 mg (about 0.2 mmol) of 1,1'-bis(p-bromophenyl)ferrocene, about 97 mg (about 0.2 mmol) of 9,9-di(2'-ethylhexyl)fluorene-2,7-diboronic acid and about 2.3 mg (about 1 mol %) of tetrakis(triphenylphosphine)palladium were placed in a flask. After a reflux condenser was connected to the flask, about 1 ml of toluene as a solvent and about 1 ml of tetraethylammonium hydroxide (about 1.33 M) were injected into the flask using a syringe under a nitrogen atmosphere.

The reaction solution was degassed with nitrogen, and refluxed in an oil bath. The reaction was allowed to proceed for about 4 days. The resulting reaction solution was diluted with about 10 ml of methylene chloride and neutralized with a saturated aqueous solution of ammonium chloride. The neutralized solution was transferred to a separatory funnel, followed by phase separation. The obtained organic layer was dried over anhydrous magnesium sulfate and passed through a glass filter to obtain a transparent polymer solution. The polymer solution was evaporated under reduced pressure to remove the solvents. The concentrated polymer solution was slowly added dropwise to vigorously stirring methanol to precipitate an orange solid, filtered, and washed with methanol several times, yielding the ferrocene-containing polymer (about 127 mg) of Formula 5 as a solid.

$^1$H NMR (300 MHz, CDCl$_3$) δ 7.7 (2H, br), 7.6 (2H, s), 7.5 (6H, br), 7.4 (4H, br), 4.6 (4H, s), 4.3 (4H, s), 2.1 (4H, s). 0.9 (14H, br), 0.7 (14H, br) THF-SEC (relative to PS standards) M$_n$: 10,000 g/mol, PDI: 1.95

Preparative Example 2

About 293 mg (about 0.51 mmol) of 1,4-bis(diethyl(2,5-hexyloxy)benzylphosphonate) was placed in a flask, and then about 0.5 ml of THF as a solvent was added thereto under a nitrogen atmosphere. To the mixture was slowly added about 1.3 ml of a solution (about 1 M) of potassium t-butoxide in THF at about 0° C. After stirring for about 30 minutes, a solution (1 ml) of 1,1-ferrocene dicarboxyaldehyde (122 mg) was slowly injected into the mixture. The reaction was allowed to proceed for about 12 hours. The reaction solution was diluted with about 10 ml of methylene chloride and neutralized with a saturated aqueous solution of ammonium chloride. The neutralized solution was transferred to a separatory funnel, followed by phase separation. The obtained organic layer was dried over anhydrous magnesium sulfate and passed through a glass filter to obtain a transparent polymer solution. The polymer solution was evaporated under reduced pressure to remove the solvents. The concentrated polymer solution was slowly added dropwise to vigorously stirring methanol to precipitate a red solid, filtered, and washed with methanol several times, yielding the ferrocene-containing polymer (about 225 mg) of Formula 6 as a solid.

$^1$H NMR (300 MHz, CDCl$_3$) δ 7.0 (2H, br), 6.8 (2H, br), 4.5 (4H, s), 4.3 (4H, s), 3.7 (4H, br), 1.8 (4H, br). 1.4 (12H, br), 0.9 (6H, br) THF-SEC (relative to PS standards) M$_n$: 2,200 g/mol, PDI: 3.31

Preparative Example 3

About 92 mg (about 0.39 mmol) of 1,1-divinyl ferrocene, about 214 mg (about 0.39 mmol) of 1,4-bis(2-ethylhexyl)-2,5-diiodobenzene, about 1.8 mg (about 2 mol %) of palladium acetate and about 6 mg (about 5 mol %) of tri(o-tolyl)phosphine were placed in a flask. After a reflux condenser was connected to the flask, about 1.5 ml of 1,4-dioxane as a solvent and about 230 μl (about 1 mmol) of tributyl amine as a base were injected into the flask using a syringe under a nitrogen atmosphere. The reaction was allowed to proceed for about 24 hours. The reaction solution was diluted with about 10 ml of methylene chloride and neutralized with a saturated aqueous solution of ammonium chloride. The neutralized solution was transferred to a separatory funnel, followed by phase separation.

The obtained organic layer was dried over anhydrous magnesium sulfate and passed through a glass filter to obtain a transparent polymer solution. The polymer solution was evaporated under reduced pressure to remove the solvents. The concentrated polymer solution was slowly added dropwise to vigorously stirring methanol to precipitate an orange solid, filtered, and washed with methanol several times, yielding the ferrocene-containing polymer (194 mg) of Formula 7 as a solid.

$^1$H NMR (300 MHz, CDCl$_3$) δ 7.3 (2H, br), 6.9 (2H, br), 6.7 (2H, br), 4.4 (4H, s), 4.3 (4H, s), 2.6 (4H, br), 1.6 (2H, br). 1.4 (16H, br), 0.9 (12H, br) THF-SEC (relative to PS standards) M$_n$: 6,300 g/mol, PDI: 2.26

Example 1

Al was deposited to a thickness of about 80 nm on a glass substrate (about 0.3 mm×about 1 mm) by thermal evaporation to form a lower electrode. About 10 mg of the ferrocene-containing polymer prepared in Preparative Example 1 was dissolved in about 1 ml of chloroform (CHCl$_3$) by sonication for about 15 minutes. The resulting solution was passed through a syringe filter (pore size: about 0.2 μm) made of PTFE, and spin-coated at about 2,000 rpm on the lower substrate for about 20 seconds. The remaining solvent was removed by baking the coated substrate on a hot plate at about 65° C. for about 10 minutes to form an organic active layer. LiF was deposited to a thickness of about 6 nm on the organic active layer to form a barrier layer, and thereafter, Cu was deposited to a thickness of about 80 nm on the barrier layer to form an upper electrode, completing fabrication of an organic memory device according to example embodiments. The thickness of the organic active layer was controlled within about 50 nm to about 100 nm, as measured using an Alpha-Step™ profilometer. The thickness of the deposited electrodes was controlled using a quartz crystal monitor.

Test Example 1

Test for Switching Characteristics of Memory Device

Figure 4:
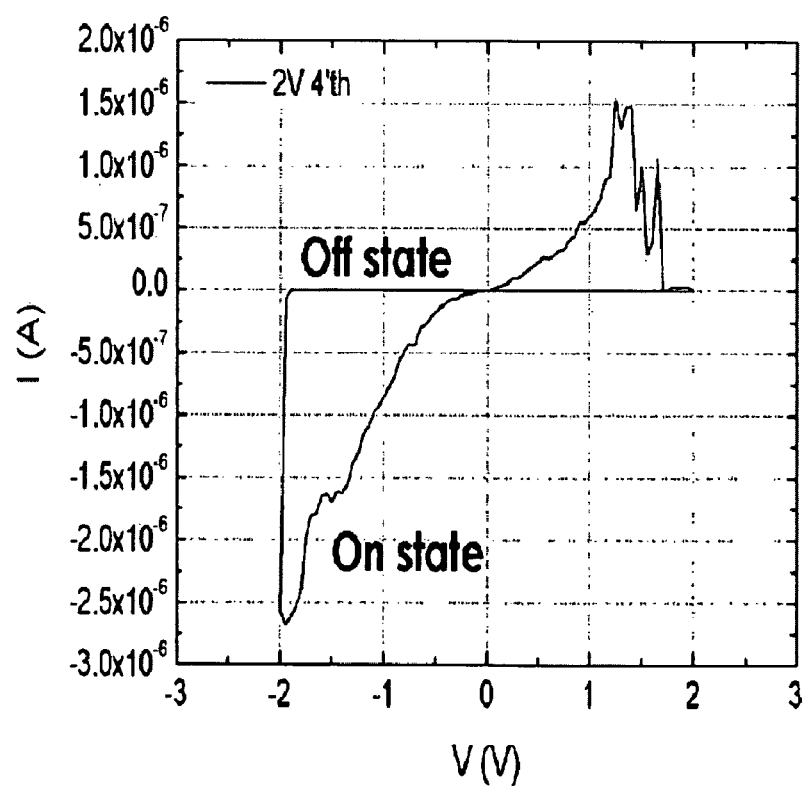
Figure 5:
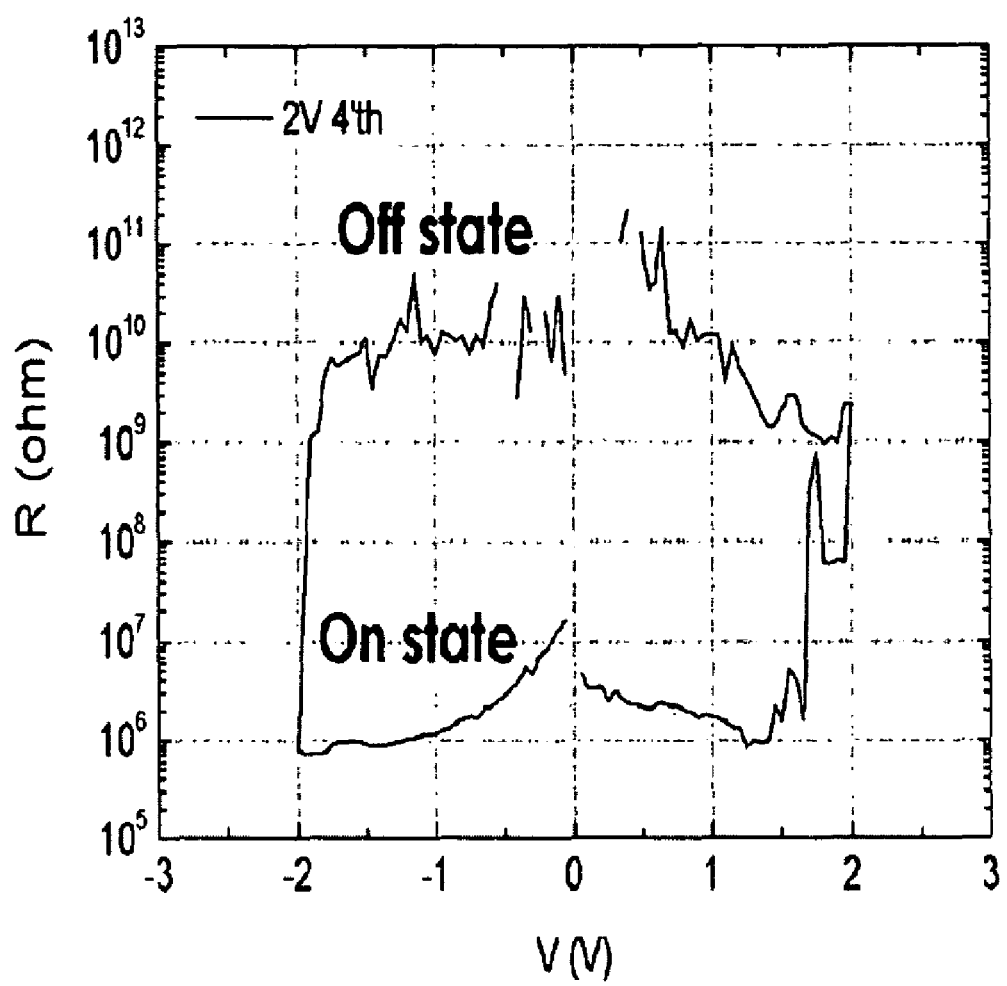

The electrical properties of the memory device fabricated in Example 1 were evaluated using a Keithley 2400 Source Meter. After a voltage was applied to the memory device, the switching properties of the memory device were evaluated as changes in current and the obtained results are shown in FIG. 4. The changes in resistance were measured in response to the applied voltage, and the results are shown in FIG. 5. The voltage was applied at a sweep speed of about 5 mV/s from about +1/−1 V to about +5/−5V.

Referring to FIG. 4, the memory device showed two conductive states when the voltage was swept in both directions. Where sweeping was carried out by the application of a positive voltage, the memory device becomes a higher resistance state (e.g. an "OFF" state). Where a negative bias voltage was applied, the memory device was switched into a lower resistance state (e.g. an "ON" state). From the graph shown in FIG. 4, the organic memory device, which may include the ferrocene-containing polymer of example embodiments, was switched between the higher resistance state and the lower resistance state, depending on the applied voltage. Each of the two different resistance states may be maintained for an increased period of time even when no voltage or current was applied to the memory device. Because the resistance states may be read by detecting a current flowing when a lower voltage is applied, the device of example embodiments may be useful as a memory device.

As apparent from the above description, because the ferrocene-containing polymers of example embodiments have multiple oxidation states, they may be used as materials for organic active layers of memory devices to provide bistability characteristics to the memory devices.

When compared to inorganic memory devices, the organic memory devices of example embodiments may offer the following advantageous effects: miniaturization, decreased switching time, decreased operating voltage, decreased fabrication costs, and increased reliability. Based on these advantages, the organic memory devices of example embodiments may be used as light-weight, highly integrated, large-capacity memory devices.

Furthermore, because the organic memory devices of example embodiments may be fabricated by a simpler and economical process, e.g., spin casting and/or spin coating, and may be processed at decreased temperatures, they may be applied to flexible memory devices.

Although example embodiments have been disclosed for illustrative purposes, those skilled in the art will appreciate that various modifications and variations are possible, without departing from the scope and spirit of the appended claims. Accordingly, such modifications and variations are intended to come within the scope of the claims.

What is claimed is:

1. A ferrocene-containing homopolymer comprising a structure represented by one of Formulae 5 to 7 below:

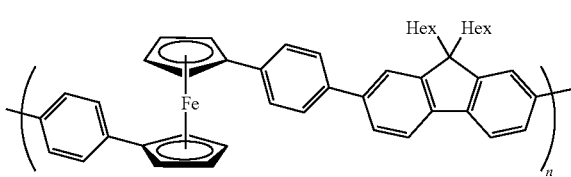

(5)

wherein Hex represents a hexyl group and n is from 1 to 1000;

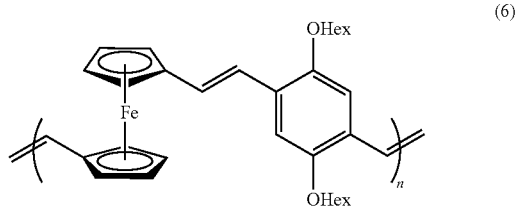

(6)

wherein Hex represents a hexyl group and n is from 1 to 1000; and

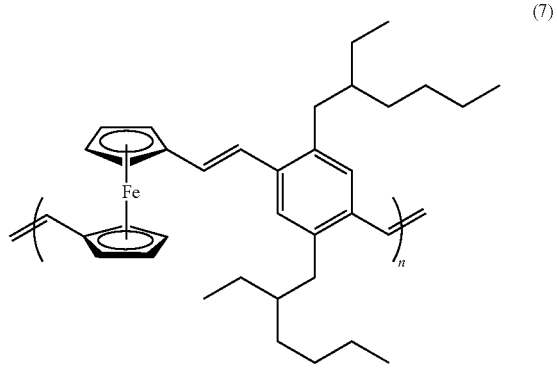

(7)

wherein n is from 1 to 1000.

2. An organic memory device comprising the ferrocene-containing homopolymer according to claim 1.

3. The organic memory device according to claim 2, wherein the organic memory device comprises:

a first electrode;
an organic active layer formed of the ferrocene-containing polymer; and
a second electrode.

4. The organic memory device according to claim 3, wherein the first electrode and the second electrode are made of at least one material selected from the group consisting of metals, metal alloys, metal nitrides, metal oxides, metal sulfides, conductive polymers, organic conductors, nanostructures, and crystals.

5. The organic memory device according to claim 4, wherein the first electrode and the second electrode are made of at least one material selected from the group consisting of gold, silver, platinum, copper, cobalt, nickel, tin, titanium, tungsten, aluminum, and indium tin oxide.

6. The organic memory device according to claim 3, further comprising:

a barrier layer formed under the first electrode or on the second electrode.

7. The organic memory device according to claim 6, wherein the barrier layer is formed of an inorganic material selected from the group consisting of oxides of Si, Al, Nb, Ti, Cr, V, Ta, Cu, Mg, W and AlN, or an organic material selected from the group consisting of Tris(8-hydroxyquinolinato)aluminum (Alq3), polymethylmethacrylate, polystyrene and PET.

8. The organic memory device according to claim 7, wherein the barrier layer is formed of a material selected from the group consisting of $SiO_2$, $Al_2O_3$, $Cu_2O$, $TiO_2$, and $V_2O_3$.

9. A method of fabricating an organic memory device comprising:

providing a first electrode;
forming an organic active layer on the first electrode, the organic active layer being formed of a ferrocene-containing homopolymer having a structure represented by one of Formulae 5 to 7 below:

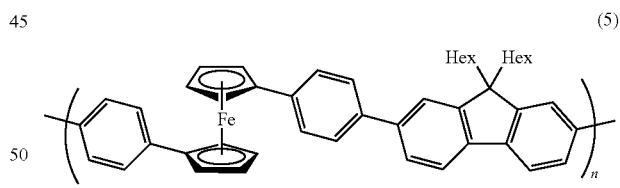

(5)

wherein Hex represents a hexyl group and n is from 1 to 1000;

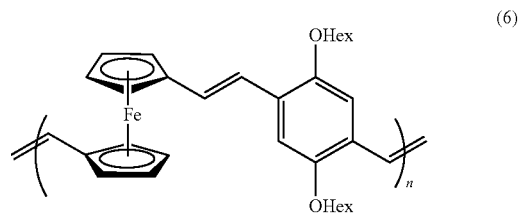

(6)

wherein Hex represents a hexyl group and n is from 1 to 1000: and

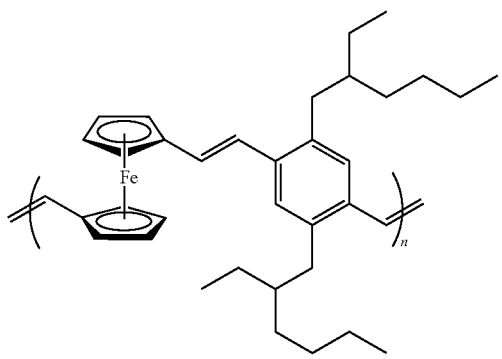

(7)

wherein n is from 1 to 1000; and forming a second electrode on the organic active layer.

10. The method according to claim 9, wherein the first electrode and the second electrode are made of at least one material selected from the group consisting of metals, metal alloys, metal nitrides, metal oxides, metal sulfides, conductive polymers, organic conductors, nanostructures, and crystals.

11. The method according to claim 10, wherein the first electrode and the second electrode are made of at least one material selected from the group consisting of gold, silver, platinum, copper, cobalt, nickel, tin, titanium, tungsten, aluminum, and indium tin oxide.

12. The method according to claim 9, further comprising:
forming a barrier layer under the first electrode or on the second electrode.

13. The method according to claim 12, wherein forming the barrier layer includes forming the barrier layer of an inorganic material selected from the group consisting of oxides of Si, Al, Nb, Ti, Cr, V, Ta, Cu, Mg, W and AlN, or an organic material selected from the group consisting of Tris(8-hydroxyquinolinato(aluminum (Alq3), polymethylmethacrylate, polystyrene and PET.

14. The method according to claim 13, wherein forming the barrier layer includes forming the barrier layer of a material selected from the group consisting of $SiO_2$, $Al_2O_3$, $Cu_2O$, $TiO_2$, and $V_2O_3$.

* * * * *